US011389470B2

(12) United States Patent
Clement et al.

(10) Patent No.: US 11,389,470 B2
(45) Date of Patent: Jul. 19, 2022

(54) COMPOSITIONS USEFUL FOR MUCOSAL HEALING

(71) Applicants: CENTRE NATIONAL de la RECHERCHE SCIENTIFIQUE, Paris (FR); UNIVERSITE PARIS DIDEROT, Paris (FR); INSTITUT NATIONAL de la SANTE ET DE LA RECHERCHE MEDICALE, Paris (FR); UNIVERSITE PARIS DESCARTES, Paris (FR); ASSISTANCE PUBLIQUE-HOPITAUX de PARIS, Paris (FR)

(72) Inventors: Olivier Clement, Paris (FR); Christophe Cellier, Paris (FR); Claire Wilhelm, Vélizy-Villacoublay (FR); Florence Gazeau, Le Kremlin Bicêtre (FR); Amanda Brun, Igny (FR); Gabriel Rahmi, Paris (FR)

(73) Assignees: CENTRE NATIONAL DE LA RECHERCHE SCIENTIFIQUE, Paris (FR); UNIVERSITÉ PARIS CITÉ, Paris (FR); INSTITUT NATIONAL DE LA SANTE ET DE LA RECHERCHE MEDICALE, Paris (FR); ASSISTANCE PUBLIQUE-HOPITAUX DE PARIS, Paris (FR)

( * ) Notice: Subject to any disclaimer, the term of this patent is extended or adjusted under 35 U.S.C. 154(b) by 0 days.

(21) Appl. No.: 16/317,615

(22) PCT Filed: Jul. 11, 2017

(86) PCT No.: PCT/EP2017/067374
§ 371 (c)(1),
(2) Date: Jan. 14, 2019

(87) PCT Pub. No.: WO2018/011192
PCT Pub. Date: Jan. 18, 2018

(65) Prior Publication Data
US 2019/0282609 A1    Sep. 19, 2019

(30) Foreign Application Priority Data

Jul. 12, 2016  (EP) .................... 16305879

(51) Int. Cl.
*A61K 31/77* (2006.01)
*A61K 9/06* (2006.01)
*A61K 9/127* (2006.01)
*A61P 1/04* (2006.01)
*A61K 35/28* (2015.01)

(52) U.S. Cl.
CPC ............... *A61K 31/77* (2013.01); *A61K 9/06* (2013.01); *A61K 9/127* (2013.01); *A61K 35/28* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 7,083,806 B2 * | 8/2006 | Rippon | A61K 9/0014 424/484 |
| 8,658,139 B1 | 2/2014 | Cutler | |
| 9,226,996 B2 * | 1/2016 | Moro | A61K 47/10 |
| 9,759,715 B2 * | 9/2017 | Smith | A61L 31/145 |
| 10,561,680 B2 * | 2/2020 | Lorenzo-Z niga Garcia | A61L 24/043 |
| 2002/0187107 A1 | 12/2002 | Libin | |
| 2006/0045872 A1 * | 3/2006 | Miguel | A61P 27/16 424/93.7 |
| 2010/0183519 A1 * | 7/2010 | Katz | A61P 17/02 424/9.2 |
| 2014/0336131 A1 | 11/2014 | Savage et al. | |
| 2015/0174196 A1 * | 6/2015 | Gourdie | C07K 7/08 424/422 |

FOREIGN PATENT DOCUMENTS

| DE | 102005030492 | 1/2007 |
|---|---|---|
| WO | 9742962 | 11/1997 |

OTHER PUBLICATIONS

Nawaz et al. "Extracellular Vesicles: Evolving Factors in Stem Cell Biology" (published Nov. 16, 2015). https://www.ncbi.nlm.nih.gov/pmc/articles/PMC4663346/.*
Volpe et al. "Mesenchymal stromal cells from adipose tissue attached to suture material enhance the closure of enterocutaneous fistulas in rat model" 2014.*
Accardo, Antonella et al., "Structural Insights On Nanoparticles Containing Gadolinium Complexes as Potential Theranostic," Colloid & Polymer Science, Springer Verlag, Heidelberg, DE, vol. 292, No. 5, Jan. 18, 2014, pp. 1121-1127.
Jahn et al., "AAPE Proliposomes for Topical Atopic Dermatitis Treatment," Elsevier Science Publishers, Amsterdam, Dec. 12, 2014.

(Continued)

*Primary Examiner* — Danah Al-Awadi
(74) *Attorney, Agent, or Firm* — Wolter VanDyke Davis PLLC; Michael Byrne (57) ABSTRACT

The present invention relates to a composition comprising at least one poloxamer compound for use in the treatment of a fistula in an individual.

7 Claims, 6 Drawing Sheets

(56) References Cited

OTHER PUBLICATIONS

Wang et al., Support of Human Adipose-Derived Mesenchymal Stem Cell Multipotency by a Poloxamer-Octapeptide Hybrid Hydrogel,II Biomaterials, Elsevier Science Publishers Barking, GB, vol. 31, No. 19, Jul. 1, 2010, pp. 5122-5130.
Tarnawski et al., "Protection of the Rat Gastric Mucosa Against Aspirin Injury by Arachidonic Acid: A Dietary Prostaglandin Precursor Fatty Acid," European Journal of Clinical Investigation, vol. 19, No. 3, Jun. 1, 1989, pp. 278-290.
International Search Report, dated Oct. 17, 2017.

\* cited by examiner

COMPOSITIONS USEFUL FOR MUCOSAL HEALING

CROSS-REFERENCE TO RELATED APPLICATIONS

This application is a U.S. national phase of International Application No. PCT/EP2017/067374 filed Jul. 11, 2017, which claims the benefit of French Application No. 16305879.5 filed Jul. 12, 2016, the entire contents of which are hereby incorporated by reference.

FIELD OF THE INVENTION

The invention relates to compounds and compositions useful for mucosal healing, in particular for the treatment of fistulae in an individual.

BACKGROUND OF THE INVENTION

The mucosa is a specific membrane which lines the cavities opened to the outside environment, particularly to the outside of the body. Thus, mucosa notably comprises the digestive tract, the respiratory tract, the urinary tract and the genital tract. The mucosae are the target of numerous injuries and healing is rendered difficult because of the moist environment.

Mucosal healing failure can be encountered in two abnormal inflammatory situations: stenosis and fistula.

A stenosis is a permanent narrowing of the lumen of a structure such as a digestive conduit or an organ. The occurrence of stenosis is in particular very common in patients after an extended endoscopic resection of a superficial tumour. By way of example, oesophageal stenosis is responsible for dysphagia and vomiting. (Ono et al. (2009) *Gastrointest. Endosc.* 70:860-866, Ohki et al. (2012) *Gastroenterology* 143:582-588.e1-2).

A fistula is a mucosal injury characterized by an abnormal connection between a cavity or an organ, with another, or with the outside of the body. It is usually the result of an injury or a surgical complication. In addition, infections and inflammations can also be the cause of fistulae. Fistulae also occur in Crohn's disease, a chronic inflammatory bowel disease (IBD).

The connection can occur in various parts of the body and after various surgical techniques such as digestive, thoracic or gynaecological surgery. By way of example, an enterocutaneous fistula (ECF) is a digestive fistula which results from an abnormal communication between the small or the large bowel and the skin. About 75% to 85% of ECF are postoperative and account for significant mortality (6 to 33%) due to sepsis, nutritional abnormalities and electrolyte imbalances.

Few studies are available in the literature regarding fistula treatment and stenosis prevention, and the results are not consensual.

Stenosis occurs particularly after extended mucosal resection. Most of the treatments to prevent such stenosis consist in administration of pharmacological agents such as glucocorticoids or antineoplastic drugs or in physical techniques such as balloon dilatation or bougienage. However, no such treatment strategies are now recognized as fully effective in preventing stenosis (Wen et al. (2014) *Gastroenterology Research and Practice*, 2014).

Sclerosing agents, such as polidocanol, or biological glues, such as fibrin sealant, have been used to treat fistulae (Barthelemy et al. (1989) *Acta Endoscopia* 19:269-274). However, several sessions of injection are usually required.

Alternatively, endoscopic clips or stent are used for the treatment of digestive fistulae during an endoscopic procedure (e.g. gastroscopy or colonoscopy). Despite a high fistula healing rate, the results are quite disappointing because stents related complications are abdominal pain, digestive perforation and stent migration. Moreover, the associated total hospital stay is very long leading to high costs (Christophorou et al. (2015) *Endoscopy*. 47:988-96).

Eventually, the injection of sclerosing agents or the introduction of endoscopic clips or stents can be used only with small fistulae (less than 10 mm of diameter).

Thus, treatment with such agents or endoscopic clips or stents do not allow for durable fistula closing and treatments for fistula closure are still subject to too slow healing and a high failure rate, especially in patients with co-morbid conditions.

Accordingly, there is a need for alternative therapeutic strategies, which would lead to improved mucosal healing.

In addition, it is also highly necessary to find an effective prevention of stenosis, in particular after extended endoscopic mucosal resection.

SUMMARY OF THE INVENTION

The present invention arises from the unexpected finding, by the inventors, that poloxamer, optionally associated to a mesenchymal stem cell-derived product, promotes mucosal healing.

Thus, the present invention relates to a composition comprising at least one poloxamer compound, in particular as active ingredient, for use in mucosal healing in an individual.

In an embodiment of the invention, the above-defined composition further comprises at least one stem cell-derived product.

In another embodiment of the invention, the above-defined composition further comprises at least one contrast agent.

In another embodiment of the invention, the above-defined composition is a medical device or a pharmaceutical composition.

The present invention further relates to a poloxamer compound for use in mucosal healing, in particular for use in the treatment of a fistula or for use in the prevention of stenosis, in an individual.

In an embodiment of the invention, the above-defined poloxamer compound for use in mucosal healing, in particular in the treatment of a fistula, or the prevention of stenosis, is combined with at least one stem cell-derived product and/or at least one contrast agent.

The invention also relates to the above-defined poloxamer compound for use in mucosal healing, in particular in the treatment of a fistula, or the prevention of stenosis, further comprising placing a stent or a clip.

The present invention also relates to a pharmaceutical composition comprising at least one poloxamer compound, in particular as active ingredient, and/or at least one stem cell-derived product, in particular as active ingredient, and/or at least one contrast agent, optionally associated to a pharmaceutically acceptable carrier or excipient.

The invention also relates to products containing:
at least one poloxamer compound, and
at least one stem cell-derived product and/or at least one contrast agent, as a combined preparation for simultaneous, separate or sequential use in mucosal healings.

The invention also relates to a kit comprising:
a composition comprising at least one poloxamer compound, and
at least one means for endoscopic administration of the composition in a mucosal injury, and
optionally at least one contrast agent and/or at least one stem cell-derived product.

DETAILED DESCRIPTION OF THE INVENTION

As intended herein, the term "comprising" has the meaning of "including" or "containing", which means that when an object "comprises" one or several elements, other elements than those mentioned may also be included in the object. In contrast, when an object is said to "consist of" one or several elements, the object cannot include other elements than those mentioned.

Mucosal Healing

As intended herein, "mucosal healing" relates to the partial or complete restoration of the integrity of a mucosa or a mucosal tissue after a mucosal injury, such as a wound, an ulceration, a perforation, an inflammation or a lesion.

As should be clear to one of skill in the art, a "mucosa" or "mucosal tissue" relates to moist epithelium layer(s) which line body cavities and surround internal organs.

Mucosal tissues are well known to one of skill in the art and can be of any type. However it is preferred that mucosal tissues according to the invention are selected form the group consisting of the respiratory mucosa, the digestive mucosa, the anoperineal mucosa and the urogenital mucosa. More preferably, mucosal tissues according to the invention are selected from the group consisting of the bronchial mucosa, tracheal mucosa, nasal mucosa, oral mucosa, pharynx mucosa, oesophageal mucosa, gastric mucosa, intestinal mucosa, in particular the duodenal, jejunal, ileal, colon, rectal, anal mucosa, urethral mucosa, penile mucosa, endometrium, vaginal mucosa.

Mucosal injuries which can be healed or prevented according to the invention are preferably selected from the group consisting of fistula, in particular post-operative fistula and stenosis in particular post-operative or post-resection stenosis.

Fistulae are well known to the one of skill in the art and are notably defined in the 10$^{th}$ revision of the International Classification of Diseases (ICD-10) 2016 version by the World Health Organization. By way of example, fistulae according to the invention can be:
fistulae of intestine, defined in class K63.2 ICD-10,
fistulae involving female urinary-genital tract, defined in class N82 ICD-10,
fistula of stomach and duodenum, defined in class K31.6 ICD-10,
fistulae of gallbladder, defined in class K82.3 ICD-10,
fistulae of anal and rectal region, defined in class K60 ICD-10,
urethral fistulae, defined in class N36 ICD-10
fistulae of appendix, defined in class K38.3 ICD-10
fistulae of bile duct, defined in class K83.3 ICD-10
vesico-intestinal fistulae, defined in class N32.1 ICD-10
vesical fistulae, defined in class N32.2 ICD-10.

Fistulae which can be treated according to the invention are preferably selected from the group consisting of digestive fistula, respiratory fistula, urogenital fistula, anoperineal fistula and inflammatory fistula, in particular in post-operative fistulae or in autoimmune or inflammatory diseases, such as Crohn's disease.

In particular, the fistula which can be treated according to the invention is an entero-cutaneous fistula or an oesophageal fistula.

Stenosis are well known to one of skill in the art and are notably defined in the 10$^{th}$ revision of the International Classification of Diseases (ICD-10) 2016 version by the World Health Organization. By way of example, stenosis according to the invention can be:
stenosis of anus and rectum, defined in class K62.4 ICD-10, or
stenosis of oesophagus, defined in class K22.2 ICD-10.

In an embodiment of the invention, the stenosis which can be prevented or treated according to the invention is a post-resection or a post-operation (i.e. a post-surgical operation) stenosis. By way of example, the post-resection or post-operation stenosis may follow from a resection, in particular an extended endoscopic resection, of a superficial tumor, such as a superficial adenocarcinoma or squamous cell carcinoma.

In another embodiment of the invention, the stenosis which can be prevented or treated according to the invention preferably result from a caustic ingestion, such as an accidental acidic intake or an over-ingestion of soda.

In still another embodiment of the invention, the stenosis which can be prevented or treated according to the invention preferably result from mucosal lesions in inflammatory diseases, and mucosal lesions after drugs intake.

More preferably, the stenosis which can be prevented or treated according to the invention is a post-resection stenosis, in particular an oesophageal post-resection stenosis.

Individual

As intended herein, the individual is preferably a mammal and more preferably a human.

In an embodiment, the individual according to the invention has one or more postoperative mucosal injuries. Preferably, the individual according to the invention suffers from one or more gastro-intestinal surgery complications, more preferably a fistula, or presents a risk of developing stenosis. More preferably, the individual according to the invention has undergone an esophagectomy or suffers from bariatric surgery complications.

In another embodiment of the invention, the individual suffers from a post-operative fistula or an auto-immune disease. The individual according to the invention may also suffer from an inflammatory bowel disease, such as ulcerative colitis or Crohn's disease. In another aspect of the invention, the individual is infected by the human immunodeficiency virus (HIV).

In another embodiment of the invention, the individual is a woman with an obstetric fistula.

In another embodiment, the individual according to the invention is at risk of developing stenosis.

In another embodiment of the invention, the individual has a superficial tumor. Preferably, the individual according to the invention suffers from a superficial tumor of the oesophagus. More preferably, the individual according to the invention is in need of an endoscopic treatment.

In yet another embodiment of the invention, the individual is at risk of oesophageal stenosis after an extended resection.

Compound of Formula (I)

As intended herein, a "poloxamer compound" is a non-ionic triblock copolymer comprising a central hydrophobic chain of polypropylene glycol and two hydrophilic chains of polyethylene glycol. Poloxamer compounds are well known to one of skill in the art and are notably disclosed in U.S. Pat. No. 3,740,421.

Preferably, the poloxamer compound according to the invention is of the following formula (I):

As will be clear to one of skill in the art a represents the number of repeats of polyethylene glycol units and b represents the number of repeats of polypropylene glycol units. Preferably, according to the invention 10≤ a≤120 and 18≤b≤67, more preferably, 91≤a≤111 and 46≤b≤66.

Preferably, the poloxamer compound of the invention is biocompatible. As intended herein "biocompatible" relate to a compound which has essentially no, minor, or no, toxic or injurious effects on a biological tissue.

Preferably, the poloxamer compound according to the invention has thermoreversible properties or is thermoresponsive. The thermoresponsive properties of poloxamers are well known to the one of skill in the art. Poloxamers exhibit a sol state in aqueous media at a temperature less than 20° C. When the temperature increases, the poloxamer aggregates into micelles due to the reduction of solubility of the hydrophobic polypropylene glycol block in the aqueous media thereby exhibiting a gel state. The gelation process is achieved by increasing the temperature above the critical gel temperature. Preferably the critical gel temperature of the poloxamer compound according to the invention is such that the poloxamer compound is under sol state at room temperature, i.e. from 17° C. to 25° C. and under gel state at the body temperature of the individual according to the invention, i.e. from 36° C. to 38° C.

The poloxamer compound according to the invention is preferably selected from the group consisting of poloxamer 124, poloxamer 188, poloxamer 237, poloxamer 407, poloxamer 184 and poloxamer 101. Most preferably, the poloxamer compound according to the invention is poloxamer 407.

Poloxamer 407 is also referred to as Pluronic® F127, PF-127 or Synperonic® PE/F127. As is known to the one of skill in the art, the values of a and b in poloxamer 407 are usually 95<a<105 and 54<b<60.

In a preferred embodiment of the invention, the poloxamer compound is comprised in the composition or the pharmaceutical composition according to the invention, or is administered according to the invention, in a concentration of at least 18% w/v, 19% w/v, 20% w/v, 21% w/v, 22% w/v, 23% w/v, 24% w/v or 25% w/v. Preferably the poloxamer compound according to the invention is comprised in the composition or the pharmaceutical composition, or is administered according to the invention, in a concentration up to 25% w/v, 26% w/v, 27% w/v, 28% w/v, 29% w/v or 30% w/v, 31% w/v, 32% w/v, 33% w/v. More preferably, the poloxamer compound according to the invention is comprised in the composition or the pharmaceutical composition according to the invention, or is administered according to the invention, in a concentration of from 20 to 30% w/v, more particularly 22 to 28% w/v, and even more particularly 24 to 26% w/v.

Stem Cell-Derived Product

As intended herein, a "stem cell-derived product" relates to any product which can be stem cells themselves, which can be obtained from stem cells or which contains stem cells secretions.

Preferably, the stem cell-derived product according to the invention is selected form the group consisting of whole stem cells, a stem cell culture, a stem cell extract, a stem cell conditioned medium and stem cell-derived extracellular vesicles. More preferably, the stem cell-derived product according to the invention consists of stem cell-derived extracellular vesicles.

Preferably, the stem cell-derived product according to the invention originates from plant stem cells or animal stem cells, in particular mammalian stem cells, such as porcine stem cells, mouse stem cells, monkey stem cells, rabbit stem cells, human stem cells. More preferably, the stem cell-derived product originates from human stem cells.

Stem cells from which the stem cell-derived product according to the present invention derive may originate from any type of organ or tissues, including brain, bone marrow, peripheral blood, blood vessels, skeletal muscle, skin, teeth, heart, gut, liver, ovarian epithelium, adipose tissue umbilical cord blood and testis. Preferably, the stem cells are selected from the group consisting of mesenchymal stem cells, hematopoietic stem cells and neural stem cells, more preferably mesenchymal stem cells.

Preferably, the stem cell-derived product according to the invention consists of mesenchymal stem cell-derived extracellular vesicles.

The process for collecting, culturing and preserving stem cells are well known to the man skilled in the art.

Stem cell extract according to the invention can be obtained by any method known in the art. Preferably stem cell extract is obtained by cell fragmentation or lysis and optionally separation of the cell extract constituents, for instance by chromatography or centrifugation.

Stem cell conditioned medium relates to any medium, such as a liquid cell culture medium, which has been in contact with stem cells, in particular for a time sufficient for the stem cells to have had a secretion activity in the medium.

Stem cell-derived extracellular vesicles according to the invention are membrane delimitated sub-cellular entities released by stem cells in a constitutive manner or in response to stress.

Stem cell-derived extracellular vesicles according to the present invention can be of any type. Preferably, stem cell-derived extracellular vesicles are selected from the group consisting of exosomes, microvesicles and apoptotic bodies.

Processes for collecting and isolating stem cell-derived extracellular vesicles are well known to one of skill in the art. Preferably, stem cell-derived extracellular vesicles are isolated by ultracentrifugation as is notably described by van der Pol et al. (2012) *Pharmacol. Rev.* 64:676-705. By way of example, a centrifugal acceleration of about 200 to 1500 g is first performed in order to remove cells and cellular debris. Then, a second centrifugation step is performed at 10,000 to 20,000 g to pellet vesicles larger than 100 nm, and a third centrifugation step at 100,000 to 200,000 g is required to pellet vesicles smaller than 100 nm.

Preferably, stem cell-derived products used in the present invention are autologous, that is they are collected from the individual to whom the stem cell-derived product is intended to be administered.

However, stem cell-derived products according to the invention can also be allogeneic, that is collected from another individual of the same species than the individual to whom the stem cell-derived product is intended to be administered, or heterologous, that is collected from another individual of another species than that of the individual to whom the stem cell-derived product is intended to be administered. Preferably, the stem cell-derived products according to the invention are heterologous.

Contrast Agent

The contrast agent according to the invention can be of any type useful to enhance the contrast of structures and fluids within the body or body parts in medical imaging.

Preferably, the contrast agent is selected from the group consisting of iron oxide nanoparticles, gadolinium-based agents, gadopentetic acid, aminodotriazote, ioxitalamate, iohexol, iopamidol, iomeprol, iopamidol, iopentol, ioversol, iopromode, iobritidol, ioxagalte, iodixanol, Lipiodol®, Xenetix®, Optiray®.

Preferably, the contrast agent is Lipiodol®. Lipiodol® is also referred to as ethiodized oil. As is known to one of skill in the art, Lipiodol® is usually an ethyl ester of iodized fatty acids from poppy seeds.

Preferably, the contrast agent is comprised in the composition or the pharmaceutical composition according to the invention, or is administered according to the invention, in a concentration of from 5 to 40% w/v or of from 5 to 50% w/v.

Medical Device

As intended herein, a "medical device" refers to any health or medical materials for use in the treatment, mitigation, diagnosis or prevention of a disease or abnormal physical condition and which does not achieve its principal intended action in or on the human or animal body by pharmacological, immunological or metabolic means, but which may be assisted in its function by such means.

Medical devices are well known to the man skilled in the art and are notably defined in article 1 of the European directive 93/42 EEC:

"Medical device" means any instrument, apparatus, appliance, software, material or other article, whether used alone or in combination, including the software intended by its manufacturer to be used specifically for diagnostic and/or therapeutic purposes and necessary for its proper application, intended by the manufacturer to be used for human beings for the purpose of:
 diagnosis, prevention, monitoring, treatment or alleviation of disease
 diagnosis, monitoring, treatment, alleviation of or compensation for an injury or handicap
 investigation, replacement or modification of the anatomy or of a physiological process
 control of conception
and which does not achieve its principal intended action in or on the human body by pharmacological, immunological or metabolic means, but which may be assisted in its function by such means.

Administration

The administration of the compound, the composition or the pharmaceutical composition as defined above can proceed by any method known in the art.

Preferably, the compound, the composition and the pharmaceutical composition according to the invention are administrated or administrable by endoscopic and percutaneous way. More preferably, the compound, the composition and the pharmaceutical composition according to the invention are administrated or administrable endoscopically.

As intended herein "combined" or "in combination" means that the compound of formula (I) as defined above, in particular poloxamer 407, is administered at the same time than another agent or product, such as the stem cell-derived product as defined above, either together, i.e. at the same administration site, or separately, or at different times, provided that the time period during which the compound of formula (I) as defined above exerts its effects on the individual and the time period during which the additional agent or product exerts its pharmacological effects on the individual, at least partially intersect.

In an embodiment of the invention, the compound, the composition and the pharmaceutical composition for use according to the invention for the treatment of fistulae or for the prevention of stenosis, further comprises placing a stent or a clip, in particular at a site of the individual's body where a fistula or a stenosis is to be treated or prevented.

As intended herein, a stent refers to a device usually metallic, presenting as a mesh and tubular in form, placed into a cavity of a human or animal organism to hold it open. Preferably, the stent according to the invention is useful for the prevention of stenosis, in particular in conduits such as the urethra or bile ducts.

As intended herein, a clip refers to a device useful for providing a mechanical, usually metallic, suture, in particular useful for the treatment of injuries such as a lesion, an ulceration, a wound or an inflammation, in particular for the endoscopic closure of gastrointestinal wall defects. Preferably, the clip according to the invention is useful for the treatment of fistulae, in particular for the closure of gastrocutaneous (GC) fistulae.

Means for Endoscopic Administration

The administration according to the invention can be performed by any means known to the man skilled in the art suitable for an endoscopic administration.

Preferably, the means for the endoscopic administration of the compound of formula (I), the composition or the pharmaceutical composition according to the invention is a flexible cannula or a catheter.

Preferably, the flexible cannula or catheter according to the invention has a diameter from 1 to 6 mm, more preferably, from 2 to 3 mm.

Preferably, the flexible cannula or catheter according to the invention has a length of at least 1600 mm.

The endoscopic, i.e. within body, tip of the flexible cannula or catheter according to the invention can be of any type known to the one of skill in the art. Preferably, the flexible cannula or catheter according to the invention has a rounded tip or a spray tip.

DESCRIPTION OF THE DRAWINGS

FIG. 1 represents the study protocol. 5 pigs were followed from surgery endoscopy at day 0 to sacrifice at day 45. Nine esophageal fistulas were surgically created by placing two catheters during 30 days into the neck of 5 pigs and randomized into control group (n=4) and treated group (gel alone n=2 and gel-EVs n=3). After catheters withdrawal, the gel was injected into the fistula. Clinical, endoscopic and radiological evaluation of fistula healing was performed at day 30 and day 45, before histological assessment.

FIGS. 4A-4D represent pictures of the histological analysis at day 45. In treated pigs (FIGS. 4A and 4B) the fistula tract was closed with very few cells and without inflammatory infiltration. In control group (FIGS. 4C and 4D) the fistula tract was opened with important inflammatory infiltration and fibrosis.

FIGS. 5A-5F represent histological and immunohistochemical fistula analyses. Investigation of the fistula tract (FIG. 5A), inflammation score (FIG. 5B) and fibrosis maximal thickness (FIG. 5C) in the gel and the gel+ EVs group compared to control according to histological analysis. Density of myofibroblasts for control, the gel and the gel+ EVs groups according to smooth muscle actin immunohistochemical staining (FIG. 5D). Density of the muscular vessels, stained by smooth muscle actin antibody, superior to 15 for the control, the gel and the gel+ EVs groups (FIG. 5E). Density of the CD31 stained vessels (capillary and muscular vessels) superior to 30.5 for the control, the gel and the gel+ EVs groups (FIG. 5F).

EXAMPLE

A. Material and Methods

1. Experimental Protocol

The local ethical committee on animal experimentation approved this study. All animals included in the study were managed according to French laws for animal use and care and according to the directives of the European Community Council.

Five adult (25-30 kg) Yucatan pigs were used for the first experiment. There were randomized into three groups as follow: control group (2 pigs), treated group with hydrogel and extracellular vesicles (gel-EVs group, 2 pigs) and treated group with hydrogel alone (gel group, 1 pig). Two surgical fistulas were created in all animals after catheter placed on both right and left side of the neck. There were 4 fistulas created in the control group, 3 fistulas in the gel-EVs group because of one early catheter migration and 2 fistulas in the gel group.

Nine adult (25-30 kg) Yucatan pigs were used for the second experiment. There were randomized into three groups as follow: control group (3 pigs), treated group with hydrogel and extracellular vesicles (gel-EVs group, 3 pigs) and treated group with hydrogel alone (gel group, 3 pigs). Two surgical fistulas were created in all animals after catheter placed on both right and left side of the neck. There were 6 fistulas created in the control group, 6 fistulas in the gel group and 5 fistulas in the gel-EVs group because of one early catheter migration resulting in a single fistula tract for one animal.

Fistula creation, radiological and endoscopic evaluation were performed under general anaesthesia after premedication (10 mg/kg of intramuscular ketamine and 8 mg/kg of intravenous propofol) and using an endotracheal tube with continuous cardio-respiratory monitoring. Anaesthesia was maintained through isoflurane 2.5% inhalation. All animals were fasted before endoscopy.

1.1. Oesophageol Fistula Creation

A combined surgical and endoscopic approach was used to create the fistula, as described in a previous study (JF-HOD, SNFGE.org «Création d'un modble de fistule oeso-cutanée chez le porc selon une technique combinée endoscopio-chirurgicale»). The first step was the skin incision and tissue dissection of the cervical neck (first the right side and then left side). After oesophageal wall incision under endoscopic control (Gastroscope EG-530WR Fujifilm, Tokyo, Japan), two plastic catheters (9-Fr and 10-Fr T-tube, Coloplast, Humlebæk, Denmark) were inserted one after another between the skin and the esophageal lumen. Catheters were tunneled subcutaneously and fixed to the skin. Analgesia after surgery was delivered by intramuscular injection of 5 mg morphine. For each pig, 3 days antibiotic prophylaxis by amoxicillin 1 g/day (Clamoxyl, GSK, Brendford, UK) was done. Liquids were authorized on day 1 after surgery and normal feeding the days after.

After one month, the catheters were easily withdrawn in all cases. External and internal fistula orifices were evaluated under general anaesthesia, respectively by clinical and endoscopic examination at day 30. A fistulography was performed at day 30 to show the fistula tract. By endoscopy, a catheter was introduced into the internal fistula orifice and contrast agent was injected under fluoroscopy control. Just after or in the same time, the contrast agent was injected through the external orifice with a 5 ml syringe.

1.2. Cell Culture

Mesenchymal stem cell derived extracellular vehicles (EVs) were obtained from adipose tissue-derived stromal cells (ADSC) isolated from the abdominal fat of 6 month-old female pig (ABCell-bio Society, Paris, France) several months before the experiments. In order to check the ADSC porcine status, a FACS analysis was performed and showed cell expression of CD 90+, CD 105+ and CD 45−, CD 31−. Cells were cultured at 37° C. and 5% CO2 with alpha minimum essential medium including 10% fetal bovine serum and 1% antibiotics (penicillin and streptomycin).

1.3. Isolation and Characterization of Extracellular Vesicles

ADSC between passages 6 to 10 were used in the experiments. Around 70 million of cells which were stressed in serum-free medium (cultured without medium) during 48 hours were obtained. The supernatant was collected, centrifuged at 2 000 G during 10 minutes to discard the pellet (cell and apoptotic body fraction) and then EVs were isolated after ultracentrifugation (100 000 G, 37500 rpm) during 12 hours for the first time and at least 2 hours. The pellet was re-suspended in buffer (PBS, pH: 7.4). In parallel, 100 µl of this solution was used for in vitro tests for vesicle characterization and quantification of EV concentration.

1.4. Extracellular Vesicle Characterization—In Situ Transmission Electron Microscopy (TEM)

In order to analyse EV size distribution and morphology, in situ TEM experiments were carried out. A JEOL ARM 200F microscope equipped with a CEOS aberration corrector for the objective lens and a cold FEG was used. All the experiments were performed with a 200 kV acceleration voltage.

1.4.1. Nanoparticle Tracking Analysis (NTA)

Suspensions containing vesicles were analyzed using a NanoSight LM10 instrument (NanoSight, Amesbury, UK) for determining EV size distribution. A monochromatic laser beam at 532 nm was applied to the dilute suspension of vesicles. A total of 10 videos of 30 s duration were acquired and particle movement was analyzed by NTA software. In the NTA software, Brownian movement is tracked and measured from frame to frame. The velocity of particle movement is used to calculate particle size by applying the two-dimensional Stokes-Einstein equation. NTA post-acquisition settings were optimized and kept constant between triplicate analysis, and each video was then analyzed to give the mean and mode vesicle size as well as an estimate of the concentration.

1.4.2. Micromagnetophoresis

In order to investigate the integrity of EVs in the presence of Pluronic® F127 gel, magnetic EVs were produced from magnetically labelled MSC. For magnetic labeling, 8 nm maghemite nanoparticles were used, synthesized by coprecipitation and stabilized in aqueous suspension by adsorption of citrate. These iron oxide nanoparticles (IONP) were dispersed in serum-free RPMI (Roswell Park Memorial Institute) medium (Sigma, France) supplemented with 5 mM citrate at a final iron concentration of 0.1 mM. BMMSC underwent a 30-minute incubation with this medium at 37° C. Cells were then rinsed twice in serum-free RPMI medium. In order to allow nanoparticle internalization, cells were incubated for 2 hours with complete medium. The trajectories of microvesicles in magnetic field gradient created by a micromagnet were analyzed using a previously published experimental set-up (Andriola Silva A K et al. (2012) Magnetophoresis at the nanoscale: tracking the magnetic targeting efficiency of nanovectors. Nanomed. 7:1713-27). Micromagnetophoresis device consisted of a glass slide/coverslip chamber integrating a 50 µm diameter nickel rod.

The nickel microrod was submitted to a 150 mT uniform magnetic field from a rectangular magnet positioned aside. Trajectories of microvesicles inserted in micromagnetophoresis chamber were observed with a 60× objective from an optical microscope (DMIRB Leica; Leica Microsystems, Germany) which was connected to a charge-coupled device camera and a computer. For micromagnetophoresis analysis, vesicles were dispersed in PBS or in a 1:1 mixture of Pluronic® F127 gel 25% and PBS. Vesicles could not be analysed when dispersed only in the gel due to gelation at room temperature which precludes vesicles to move. Vesicle integrity was attested by its attraction to the micromagnet. Indeed, disrupted vesicles having lost their magnetic cargo do not display magnetophoresis. The same applies to the cargo not enclosed in the vesicle, as it is redispersed state and the consequent Brownian motion precludes migration towards the micromagnet.

1.5. Hydrogel Formation

Pluronic® F127 (Sigma) was dissolved in sterile PBS at a 30% concentration and stirred at 4° C. for 24 h. After solubilisation, it was filtered with a 0.2 µm filter for sterilization. Then, vesicles suspended in PBS were added to the gel, which final concentration was 25% Pluronic® F127 and $1.3 \times 10^{11}$ vesicles/ml.

Different endoscopic catheters were tested to allow the passage of the Pluronic® F127 gel trough the catheter lumen without obstruction. Hence, the 6 Fr Huiregtse® guiding catheter (Cook Medical, North Carolina, USA) was found to be the most appropriate. Optionally, the X-ray contrast agent Lipiodol can be incorporated into poloxamer 407 gel.

2. Extracellular Vesicles Engraftment

In the gel-EVs group, just after catheters were withdrawn, 8 ml of liquid Pluronic® F127 were injected into the fistula: 4 ml through the internal orifice using an endoscopic catheter and 4 ml through the external orifice using a 5 ml syringe. In the gel group, 8 ml of Pluronic® F127 without any EVs were injected similarly by the internal and external orifice. In both groups, gel-EVs and gel alone, few seconds after injection the gel became solid from the liquid form. In the control group nothing was injected into the fistula after the catheters were withdrawn.

2.1. Follow Up and Evaluation after Engraftment

Figure 1:
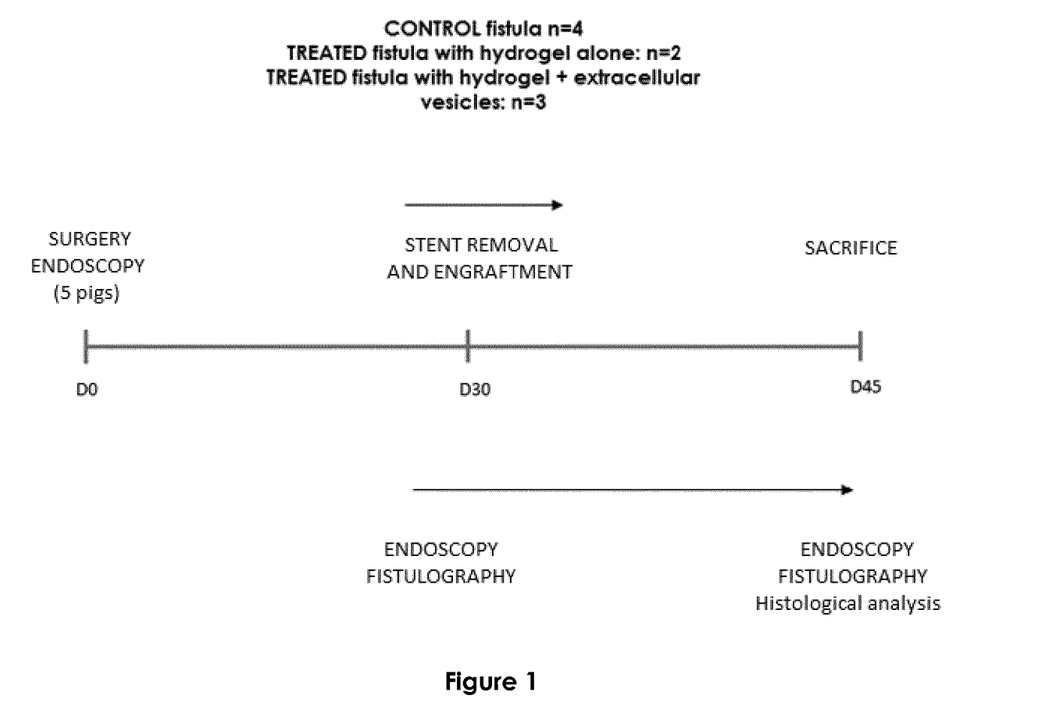

Animals were followed for 15 days after catheter withdrawal and then sacrificed (FIG. 1). On day 30 and day 45, a multimodal evaluation of the fistula under general anesthesia (clinical, endoscopic and radiologic evaluation) was performed.

2.2. Clinical Evaluation

Animals were daily examined and weighed on day 0, day 30 and day 45. Assessments of pain, behaviour, food intake, catheter positioning and external orifice fistula aspect was done. At day 30 and day 45, macroscopic aspect of the external orifice (opening and inflammation) was reported.

2.3. Endoscopic Evaluation

At day 30 and day 45, endoscopic aspect and opening of the internal orifice was noted. Catheterization of the fistula tract was systematically attempted.

2.4. Radiological Evaluation

At day 30 and day 45, radiologic evaluation (2 orthogonal incidences) was performed using a contrast agent (Xenetix® Guerbet, Villepinte, France). The most relevant incidence was kept for analysis and diameter, length and presence of abscess were reported.

3. Histological Analysis

At day 45, just after the endoscopic and radiological evaluation, pigs were scarified. A large dissection around the fistula tract including cervical oesophagus and the skin was performed for macroscopic evaluation and measurements. Specimens were harvested en-bloc and stored in 10% buffered formalin for at least 24 hours before they were embedded in paraffin and 4 µm sections were obtained, stained with hematoxylin-eosin. After the dermal and oesophageal sides were located, specific measurements were performed: presence, location and maximum thickness of fibrosis; presence of the fistula tract; presence of inflammation based on the semi quantitatively quantification of inflammatory cells; presence of re-epithelialization, necrosis or abscesses; and aspect of the vascularization around the fistula tract.

4. Immunohistochemical Analysis

Sections were fixed in fixed in 10% neutral-buffered formalin and processed for histologic examination including paraffin embedding and sectioning. Sections from selected paraffin blocks for each specimen were used for immunohistochemical analysis.

This immunohistochemical study was realized on a Ventana Roche Benchmark XT with the same antigen retrieval process, in a EDTA citrate buffer (pH 8.3) during 30 min and via the ultraView Universal DAB Detection Kit, Ventana Roche System.

Two antibodies were used:
- an anti-alpha smooth muscle actin antibody (monoclonal mouse, 1A4, DAKO), 1/500 dilution, 20 min incubation for the staining of the muscular layer of the vessels and of myofibroblasts;
- an anti-CD31/PECAM 1 antibody (monoclonal rabbit, EP78, Microm), 1/200 dilution, 32 min incubation for the staining of the endothelial layer of the vessels (capillary and muscular vessels).

5. Statistical Analysis

Statistical analysis was performed using GraphPad Prism software (Graphpad Software, La Jolla, Calif., USA). Categorical data were expressed as percentages and compared with Fischer's exact test. A p-value less than 0.05 was considered to be significant.

B. Results

1. Oesophageal Fistula Creation

In one pig, an early catheters migration occurred on the right side of the neck at day 7 following by complete scar closure and no fistula formation. Then, nine fistulas were created in the five pigs and seventeen in the nine pigs for the second experiment. The mean procedure time was 47±18 minutes. There was no intraoperative complication. Only one pig had vomiting with transient hematemesis at day 3 but evolution was rapidly favourable. In two pigs and five pigs for the second experiment, partial catheter migration was observed between day 5 and day 12 and catheters were repositioned and secured by sutures. Weight of pig was stable in the three groups without significant difference between day 0 to day 30 and day 30 to day 45.

2. Extracellular Vesicle Characterization

EVs were characterized in terms of size, morphology and integrity. EVs presented a wide size distribution with a mean hydrodynamic diameter of 175±4 nm and a mode of 138±12 nm, as determined by NTA. The same mode value was obtained from TEM analysis although the mean size of 213 nm was superior to NTA data. Mean size determined by TEM analysis is expected to be inferior to NTA one, as it does not correspond to the hydrodynamic size. Size determination by NTA may be considered more accurate as it is a high-throughput analysis based on the interrogation of thousands of events. In spite of the low statistical power for size determination, TEM analysis has the advantage to provide information on vesicle morphology. Vesicles were observed with a round regular shape presenting a wide size distribution.

In order to estimate the integrity of EVs in Pluronic® F 127 gel, vesicles were loaded with a magnetic cargo and a micromagnetophoresis analysis was performed. Vesicles could not be analyzed when dispersed only in the gel due to gelation at room temperature, which precludes vesicle movement. Instead, vesicles were dispersed in a 1:1 mixture of Pluronic® F127 gel 25% and PBS. The integrity of vesicles was qualitatively attested by their attraction to the micromagnet. Indeed, disrupted vesicles having lost their magnetic cargo do not display magnetophoresis. The same applies to the cargo not enclosed in the vesicle, as it is redispersed state and the consequent Brownian motion precludes migration towards the micromagnet. Vesicles dispersed in the mixture of Pluronic® F127 gel 25% and PBS were observed to head towards the magnet, where they were magnetically trapped, in the same way as observed for vesicles dispersed in PBS alone. This indicates that Pluronic® F127 seems not to affect the integrity of vesicles as they are able to conserve their magnetic cargo.

3. Engraftment

After successfully EVs extraction and Pluronic® F127 gel production, injection was easily performed by endoscopy into the fistula tract at day 30 after catheter withdrawal.

4. Incorporating of a Contrast Agent into the Hydrogel

Figure 6A:
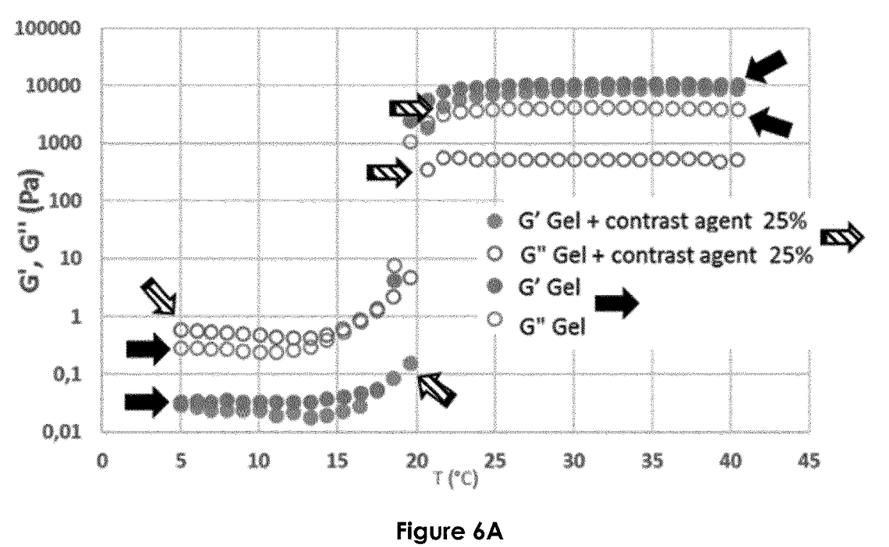
FIGS. 6A-C represent poloxamer 407 gel endowed with contrast properties while preserving its thermoresponsiveness. Rheological analysis of poloxamer 407 gel 15% with 25% of Lipiodol X-ray contrast agent (Hatched arrow) and without (Full arrow). Elastic modulus (G') and viscous modulus (G") evolution as a function of the temperature (FIG. 6A). X-ray images of poloxamer 407 gel: Lipiodol dispersions compared to gel alone and Lipiodol alone (FIG. 6B): 1- poloxamer 407 gel 20%; 2- poloxamer 407 gel 17.5%: Lipiodol 12.5%; 3-poloxamer 407 gel 15%: Lipiodol 25%; 4- poloxamer 407 gel 17.5%: Lipiodol 37.5%; 5- poloxamer 407 gel 10%: Lipiodol 50%; 6- Lipiodol 100%. X-ray images of poloxamer 407 gel 15%: Lipiodol 25% dispersion administered via the external orifice of a swine digestive fistula (FIG. 6C).
Figure 6B:
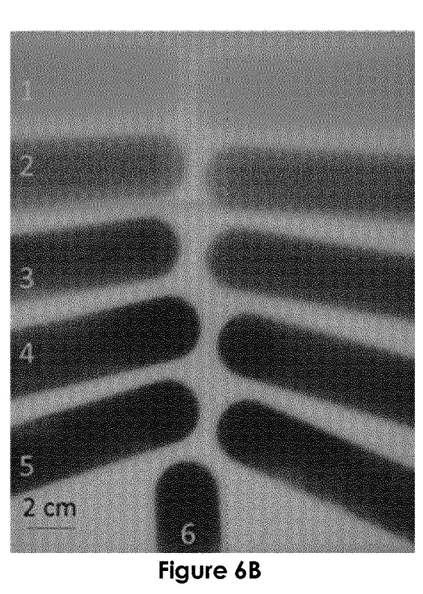
Figure 6C:
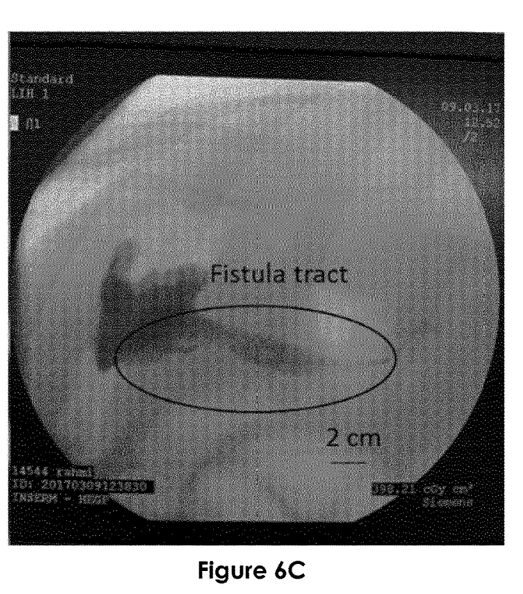

Inventors incorporated the X-ray contrast agent Lipiodol into poloxamer 407 gel (poloxamer 407 gel 15%: Lipiodol 25%). Rheological analysis showed that this product preserved poloxamer 407 gel thermoresponsiveness, featuring a sol-gel transition temperature (crossover between G' elastic modulus and G" viscous modulus) at about 20° C. (FIG. 6A). This product also presented excellent contrast properties in vitro with different concentrations. (FIG. 6B) and in vivo in a clinically-relevant swine model of digestive fistula (FIG. 6C). Preferably, the concentration of the contrast agent into the gel is 25%.

5. Follow Up and Fistula Evaluation after Engraftment

Table 1 represents the clinical, radiological and fistula characteristics at day 45 for the first experiment:

|  | Control n = 4 | Gel without vesicles n = 2 | Gel with vesicles n = 3 |
|---|---|---|---|
| Inflammatory aspect |  |  |  |
| External orifice | 4/4 | 1/2 | 0/3 |
| Internal orifice | 3/4 | 0/2 | 0/3 |
| Clinical and endoscopic fistula closure** |  |  |  |
| External orifice | 0/4 | 1/2 | 3/3 |
| Internal orifice | 0/4 | 2/2 | 3/3 |
| Radiology |  |  |  |
| Complete fistula tract | 4/4 | 0/2 (1 incomplete) | 0/3 |
| Histology |  |  |  |
| Complete fistula tract | 4/4 | 0/2 | 0/3 |
| Fibrosis | +++ | +/− | +/− |
| Inflammatory infiltration | +++ | +/− | +/− |
| Immune cells | Neutrophils | Lymphocytes | Lymphocytes |

*number of fistula
**definition of fistula closure: impossibility to gently introduce a catheter into the fistula tract

|  | Control n = 6 | Gel without vesicles n = 6 | p-value | Gel with vesicles n = 5 | p-value |
|---|---|---|---|---|---|
| Inflammatory aspect |  |  |  |  |  |
| External orifice | 6/6 | 2/6 | 0.0363 | 0/5 | 0.0009 |
| Internal orifice | 4/6 | 0/6 | 0.0143 | 0/5 | 0.0221 |
| Clinical and endoscopic fistula closure** |  |  |  |  |  |
| External orifice | 0/6 | 4/6 | 0.0363 | 5/5 | 0.0009 |
| Internal orifice | 0/6 | 6/6 | 0.0005 | 5/5 | 0.0009 |
| Radiology |  |  |  |  |  |
| Presence of fistula tract | 6/6 | 2/6 | 0.0363 | 0/5 | 0.0009 |

Figure 2:
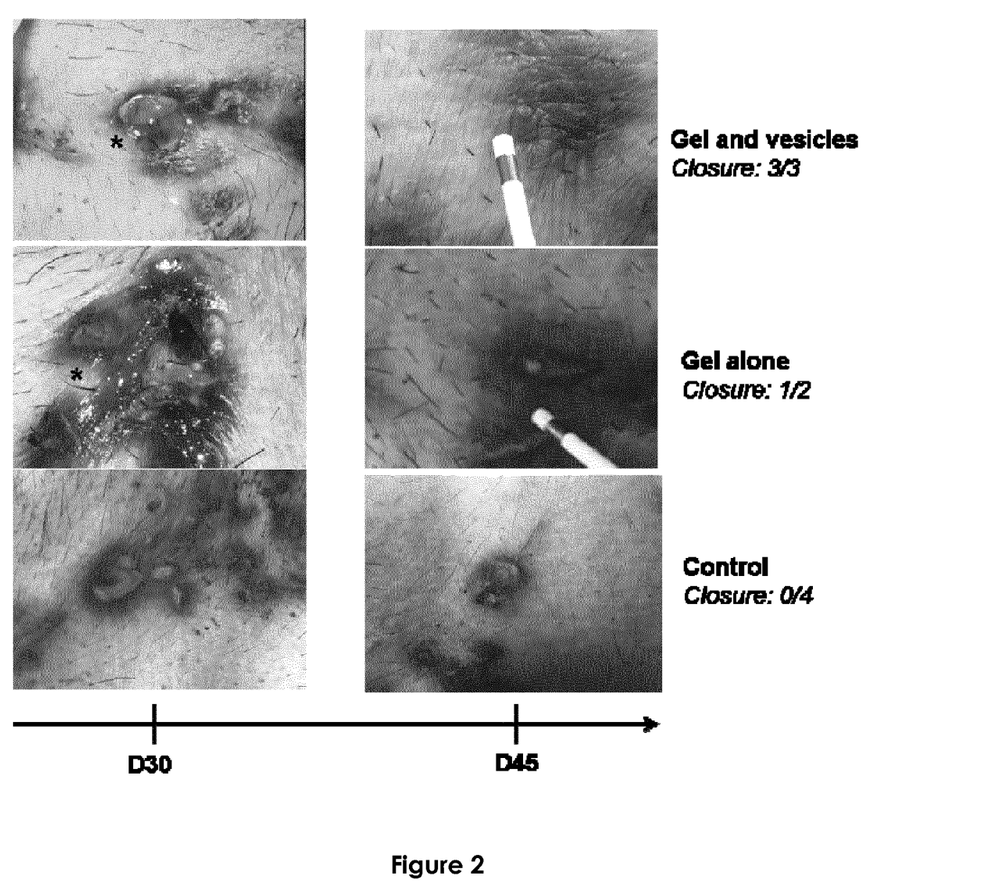
FIG. 2 represents pictures of the clinical evaluation of an exemplary fistula between day 30 and day 45 in an adult pig treated by gel and vesicles (3/3 closures observed), gel alone (1/2 closures observed) and untreated (control, 0/4 closures).

*number of fistula
**definition of fistula closure: impossibility to gently introduce a catheter into the fistula tract 5.1. Clinical Evaluation (Table 1, Table 2, FIG. 2)

First experiment: At day 30, external cutaneous orifices were open in all cases (n=9). At day 45, in control group external orifices were open in all cases (4/4). A fistulography in this group showed permeable fistula tract in all cases. In the gel-EVs group, the cutaneous orifice fistulas were closed in all cases (3/3) with homogeneous wound healing. In the gel group 1 cutaneous fistula orifice was open with a small ulceration and 1 orifice had a dot shaped aspect.

Second experiment: At D30, external fistula orifices were open featuring an inflammatory aspect in all cases (Table 2). At day 45, external fistula orifices were open and inflammatory in all cases (6 cases from 6) for the control group. A plastic catheter could be easily introduced into fistulas. The mean diameter of the external orifice in this group was 4.9±1.2 mm. For the gel group, most of external fistula orifices (4 cases from 6) were completely non-inflammatory and close. A small ulceration of less than one millimeter was noted for 2 fistula orifices. For the gel+ EVs group, the cutaneous fistula orifices were closed in all cases (5 cases from 5) and a homogeneous non-inflammatory wound healing was observed.

A statistically significant difference was observed when comparing both the gel group to the control and the gel+ EVs group to the control in terms of external fistula orifice closure and inflammatory aspect. In this regard, the analysis of the P value, the odds ratio and its 95% confidence interval are quite informative for discriminating the effect of gel versus gel+EV group. When comparing the gel group to the control and the gel+EV group to the control, P values were 0.0363 and 0.0009, respectively, indicating that the probability to obtain the same effect from the control was much higher for the gel+ EVs group than for gel group. The same applies to the analysis of the odds ratio and its 95% confidence interval. The odds ratio indicates the strength of the association between two variables estimating the likelihood of a therapy to induce an outcome of interest. Importantly, the odds ratio of 1 indicates no effect of given therapy in the outcome of interest. Therefore, the likelihood of no therapy effect may be considered inexistent only if the value 1 does not fall within the 95% confidence interval, and this was not the case to the comparison between the gel to the control group. For both the occurrence of external fistula orifice closure and the absence of an inflammatory aspect, the odds ratio when comparing the gel group to the control was 23.40 for a 95% confidence interval of 0.8925 to 613.5. Conversely, when comparing the gel+ EVs group to the control, the odds ratio was 143.0 for a 95% confidence interval of 2.413 to 8476.

A third experiment was conducted at HEGP (Georges-Pompidou European Hospital) for the treatment of one patient suffering from a colo-cutaneous fistula for whom all other therapeutic strategies failed.

The decision to test poloxamer 407 gel for this patient was accepted consensually by the staff of gastroenterology and digestive surgery services from HEGP. The off-label use of poloxamer 407 gel as a fistula occlusive for this patient complied with legal (Article L 5121-12-1 from the French code of Public Health) and ethical issues. Accordingly, the patient was informed about the risks and benefits related to the off-label use of poloxamer 407 gel as a fistula occlusive and a written consent was provided.

Poloxamer 407 gel was administered into the digestive fistula of the patient via endoscopic monitoring by a surgeon.

Three months after surgery, the clinical evaluation of the fistula of this first patient (presence of a colo-cutaneous fistula since birth) is almost closed and the flow of secretions has greatly reduced.

Figure 3:
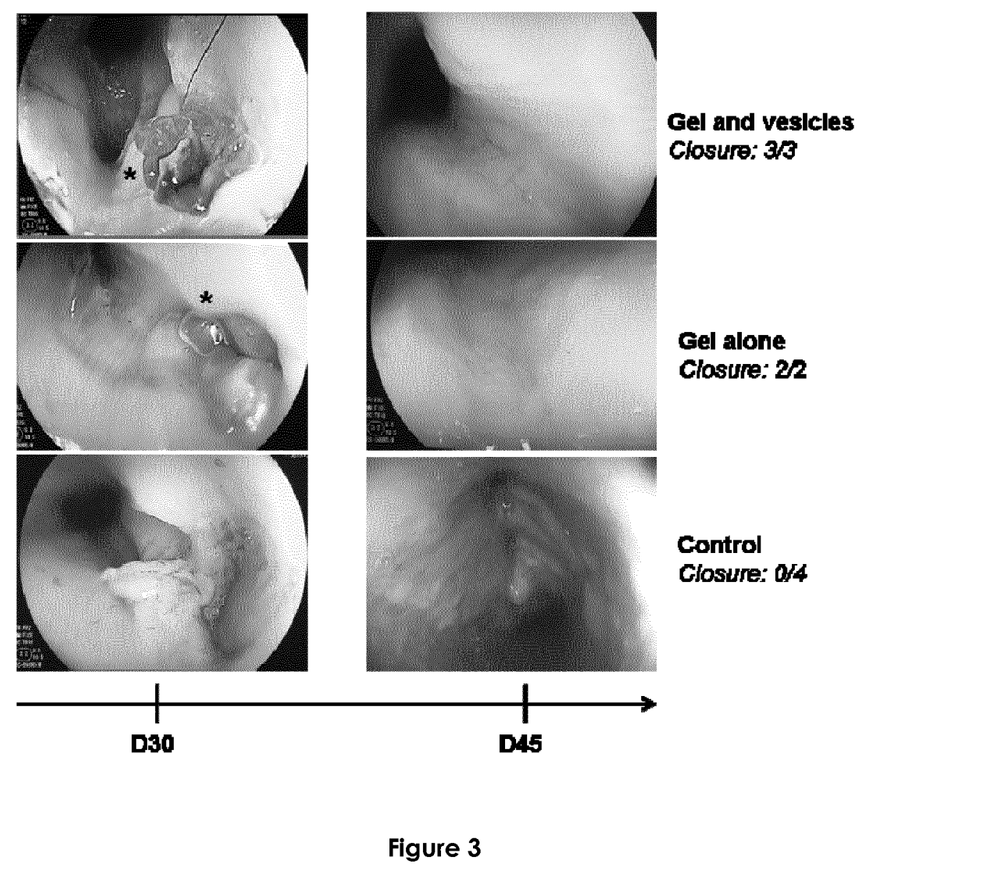
FIG. 3 represents pictures of the endoscopic evaluation of an exemplary fistula between day 30 and day 45 in an adult pig treated by gel and vesicles (3/3 closures observed), gel alone (2/2 closures observed) and untreated (control, 0/4 closures).
Figure 4A:
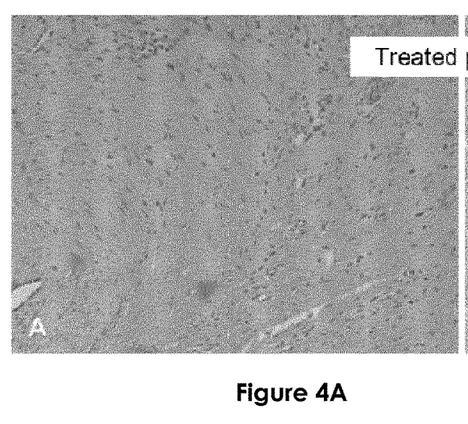
Figure 4B:
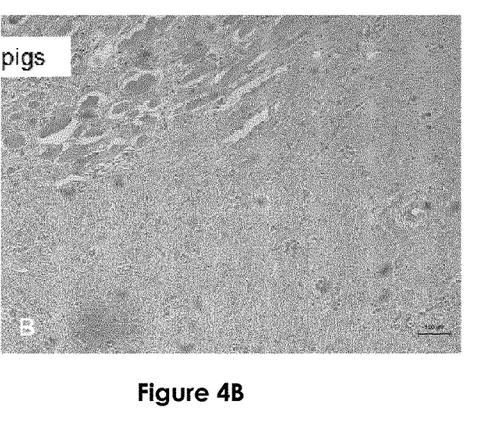
Figure 4C:
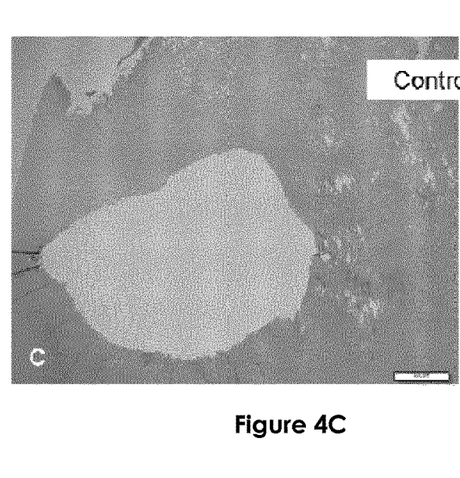
Figure 4D:
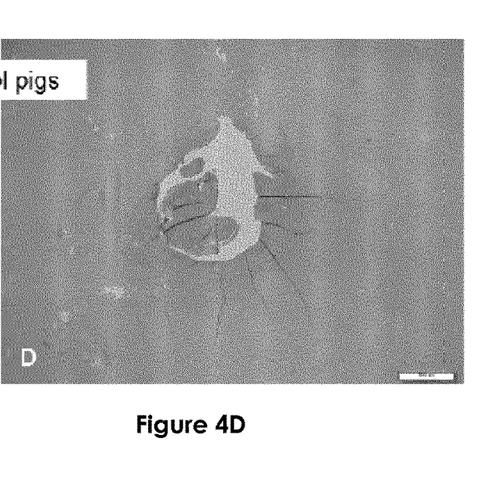

5.2. Endoscopic Evaluation (Table 1, Table 2, FIG. 3)

At day 30, in all pigs the internal orifice was open with a local inflammation and a catheter was easily introduced trough the orifice. The two internal orifices from left and the right side of the neck were quite close to each other. At day 45, in the control group, the internal orifice was re-covered with a thin layer of mucosa, easily punctured with a plastic catheter in two cases and open in two cases. In the gel and gel-EVs group, the internal orifice was closed.

A statistically significant difference was observed when comparing the gel and the gel+ EVs group to the control, both comparisons featuring similar P values, odds ratios and 95% confidence interval (Table 2).

5.3. Radiological Evaluation

First experiment: At day 30 all the fistula tracts were present after contrast agent injection either by the external or the internal orifice. There were small abscess connected to the fistula tract in the oesophageal side, both in control and treated groups. At day 45, radiological examination showed a fistula tract in all cases (4/4) in the control group. By contrast, there was no persistent fistula tract (3/3) in gel-EVs group and only a blind fistula in one case (1/2) in the gel group (Table 1).

Second experiment: At D30, all the fistula tracts were considered complete following contrast agent injection either by the external or the internal orifice. There was at least one abscess (1 to 3) connected to the fistula tract in the esophageal side, both in the control and the treated groups.

At D45, radiological examination showed a complete fistula tract in all cases (6 cases from 6) for the control group. By contrast, there was a total closure of the fistula tract in all cases for the gel+ EVs group (5 cases from 5). For the gel group, there was a total closure of the fistula tract in 4 cases and 2 cases of blind fistula (partial tract) without abscess were reported.

When comparing the gel group to the control and the gel+ EVs group to the control, P values were 0.0363 and 0.0009, respectively, indicating that the probability to obtain the same effect from control was much higher for the gel group than for the gel+ EVs group (Table 2). Besides, the odds ratio when comparing the gel group to control was 23.40 for a 95% confidence interval of 0.8925 to 613.5. Conversely, when comparing the gel+ EVs group to control, the odds ratio was 143.0 for a 95% confidence interval of 2.413 to 8476.

6. Histological immunohistochemical analysis (Table 1, Table 2, FIG. 4, FIG. 5)

First experiment: In the control group all the fistulae (4/4) were with an important acute inflammatory infiltration (neutrophils and macrophages) and necrotic areas. In all cases, there was an infiltrating fibrosis, particularly around the fistula lumen. In one case, next to the esophageal epithelium, focal re-epithelialization areas were found.

In contrast, all the fistulae were closed in the gel-EVs group (3/3).

In the gel group, 1/2 fistula was partially closed, with only one ulceration which could be found at the cutaneous side, but the fistula tract was very short; the other fistula was completely closed.

In both gel and gel-EVs groups, the fistula tract was as a thin fibrous cord and minimal inflammatory infiltration, with lymphocytes and without neutrophiles.

Figure 5A:
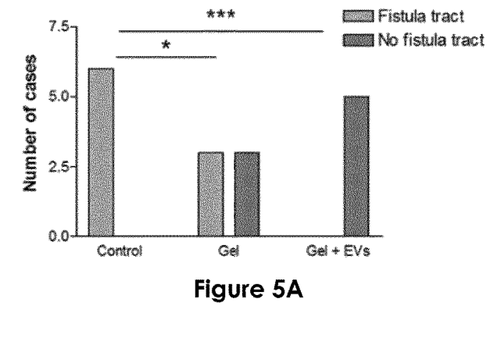

Second experiment: Histological analysis showed the presence of a fistula tract as well as the occurrence of necrotic areas in all control group cases (FIG. 5A). Conversely, all fistulas were close in the gel+ EVs group without any fistula tract. In the gel group, there was a complete closure of the fistula tract in 3 cases and a partial closure in one case. In the 2 other cases, examination showed a thin fistula tract with a small ulceration at the cutaneous side. The gel group and the more particularly the gel+ EVs group presented a statistically significant frequency of fistula closure compared to the control (FIG. 5A)).

Figure 5B:
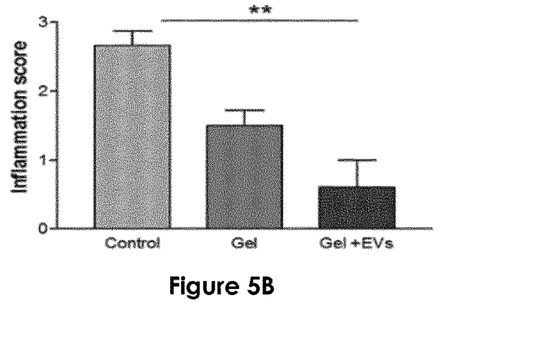
Figure 5C:
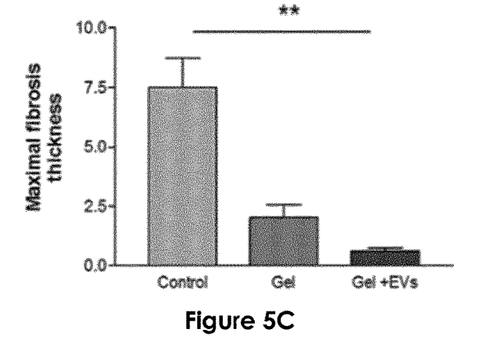

Concerning inflammation, histological data demonstrated an important neutrophile and macrophage infiltration reflecting an acute inflammation and necrotic areas in all control group cases. For the gel group and especially for the gel+ EVs group, there was a reduction in the inflammatory infiltration, with lymphocytes and without neutrophils, reflecting a more advanced healing process. A statistically significant reduction of the inflammation compared to the control was observed only for the gel+ EVs group (FIG. 5B).

Figure 5D:
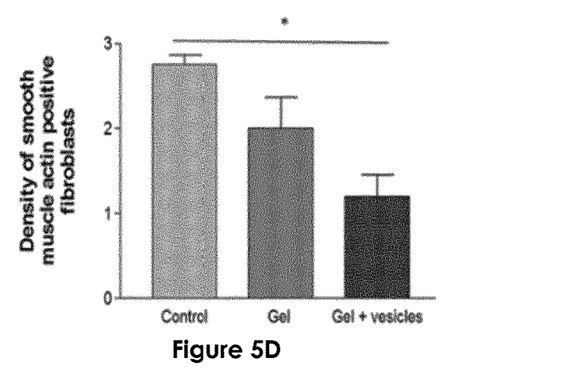
Figure 5E:
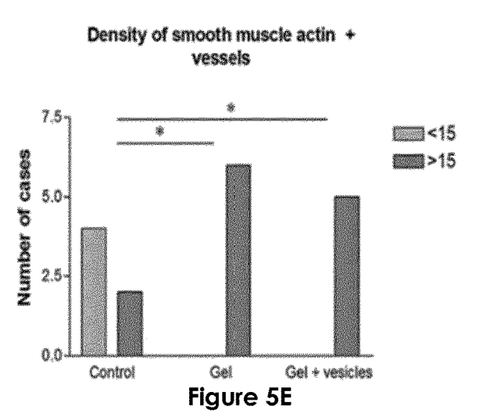
Figure 5F:
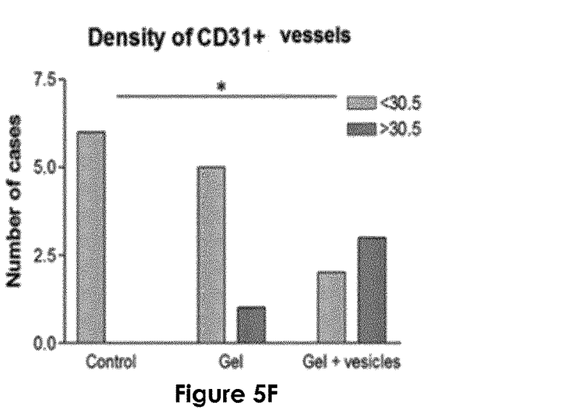

Regarding fibrosis (FIG. 5C), control group displayed an infiltrating fibrosis, particularly around the fistula lumen. In one case, next to the esophageal epithelium, focal re-epithelialization areas were found. In another case, a 10 mm abscess was contiguous to the tracheal wall. A reduction of fibrosis thickness was observed for the gel group and more importantly for the gel+ EVs group. A statistically significant reduction of fibrosis compared to the control was observed only for the gel+ EVs group. Accordingly, collagen coverage indicative of wound healing was more intensively observed for the gel+ EVs group when compared to the gel group and control. Immunohistochemistry with a smooth muscle actin antibody was investigated to access both myofibroblasts and vessels featuring a muscular wall. A statistically significant reduction in the density of myofibroblasts was observed only for the gel+ EVs group compared to the control (FIG. 5D). However, a statistically significant increase in the density of muscular vessels superior to 15 was observed for both the gel and the gel+ EVs groups compared to the control (FIG. 5E). CD31+ vascularization was equally assessed by Immunohistochemistry. A statistically significant increase in the density of CD31+ vessels (reflecting the whole vascularization) superior to 30.5 was observed for the gel+ EVs group compared to the control (FIG. 5F).

CONCLUSION

The present data show that a single topical application of Pluronic F-127 gel significantly increased fistula closure resulting in higher density of vessels featuring a muscular wall. Therefore, Pluronic F-127 may be considered more than a carrier vehicle, contributing by itself to the regenerative effect obtained in fistula healing. Importantly, the healing properties of Pluronic F-127 gel were markedly enhanced by the combination with EVs. In vivo tests evidenced a shift from 67% of complete fistula closure for the gel group to 100% for the gel+ EVs one. Besides, only the combination gel+ EVs resulted in a statistically significant (i) reduction of fibrosis, (ii) decline of inflammatory response, (iii) decrease in the density of myofibroblasts and (iv) increase of angiogenesis attested by the higher density of CD31+ vessel according to histological and immunohistochemical findings.

The invention claimed is:

1. A method for the treatment of a digestive fistula in an individual in need thereof, the method comprising administering to the individual:
   at least one mesenchymal stem cell derived extracellular vesicle; and
   a composition comprising:
   at least one poloxamer compound of formula (I):

wherein 91<a<111 and 46<b<66,
   wherein the at least one poloxamer compound is poloxamer 407,
   wherein the at least one poloxamer compound is comprised in a concentration from about 20% to about 25%,
   wherein the at least one mesenchymal stem cell derived extracellular vesicle comprises an amount of about $1.3 \times 10^{11}$ vesicles/ml,
   optionally at least one contrast agent, and
   optionally at least one pharmaceutically acceptable carrier or excipient.

2. The method according to claim 1, for the treatment of an entero-cutaneous fistula.

3. The method according to claim 1, wherein the composition is administered by endoscopy or into an external orifice.

4. A method for treatment of a digestive fistula or a mucosal injury or a stenosis in an individual in need thereof, the method comprising endoscopic administration or administration via an internal and/or external fistula orifice to the individual of:
   an effective amount of at least one mesenchymal stem cell derived extracellular vesicle; and
   a composition comprising:
   at least one poloxamer hydrogel of formula (I):

wherein 91<a<111 and 46<b<66,
   wherein the at least one poloxamer compound is poloxamer 407,
   wherein the at least one poloxamer hydrogel is comprised in a concentration from about 20% to about 25%,
   wherein the at least one mesenchymal stem cell derived extracellular vesicle comprises an amount of about $1.3 \times 10^{11}$ vesicles/ml,
   optionally at least one contrast agent,
   optionally at least one pharmaceutically acceptable carrier or excipient.

5. The method according to claim 1, wherein the at least one polyxomer is a hydrogel.

6. The method according to claim 1, wherein the at least one pharmaceutically acceptable carrier or excipient is PBS.

7. The method according to claim 1, wherein the mesenchymal stem cell derived extracellular vesicle is comprised in a mesenchymal stem cell conditioned medium.

\* \* \* \* \*